(12) United States Patent
Ryan (10) Patent No.: US 11,701,472 B2
(45) Date of Patent: Jul. 18, 2023

(54) SYRINGE STOPPER AND PLUNGER ROD ARRANGEMENT FOR A SYRINGE ASSEMBLY

(71) Applicant: Becton, Dickinson and Company, Franklin Lakes, NJ (US)

(72) Inventor: Kevin M. Ryan, Whitehouse Station, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 156 days.

(21) Appl. No.: 16/977,904

(22) PCT Filed: Mar. 14, 2019

(86) PCT No.: PCT/US2019/022300
§ 371 (c)(1),
(2) Date: Sep. 3, 2020

(87) PCT Pub. No.: WO2019/182870
PCT Pub. Date: Sep. 26, 2019

(65) Prior Publication Data
US 2021/0038823 A1 Feb. 11, 2021

Related U.S. Application Data

(60) Provisional application No. 62/645,353, filed on Mar. 20, 2018.

(51) Int. Cl.
*A61M 5/315* (2006.01)
*A61M 5/31* (2006.01)

(52) U.S. Cl.
CPC ...... *A61M 5/31501* (2013.01); *A61M 5/3135* (2013.01); *A61M 5/31513* (2013.01); *A61M 2205/0216* (2013.01)

(58) Field of Classification Search
CPC ............ A61M 5/31501; A61M 5/3135; A61M 5/31513; A61M 2205/0216;
(Continued)

(56) References Cited

U.S. PATENT DOCUMENTS 2,832,340 A * 4/1958 Dann ................. A61M 5/31511
D24/114
6,171,286 B1 1/2001 Gross
(Continued)

FOREIGN PATENT DOCUMENTS

CN 105530975 A 4/2016
EP 3042680 A1 7/2016
(Continued)

*Primary Examiner* — Katherine H Schwiker
*Assistant Examiner* — Phoebe Anne Staton
(74) *Attorney, Agent, or Firm* — The Webb Law Firm (57) ABSTRACT

A syringe assembly includes a substantially cylindrical syringe barrel including a fluid dispensing end, an open end, and at least one protrusion adjacent the open end, the at least one protrusion projecting inwardly from an inner surface of the syringe barrel, a stopper configured to be received within the open end of the syringe barrel, and a plunger rod having a plunger rod body extending along a longitudinal axis from a proximal end to a distal end and at least one support disk provided on the distal end thereof. The support disk on the plunger rod is configured to bear against the protrusion of the syringe barrel upon misalignment of the plunger rod in the syringe barrel.

16 Claims, 5 Drawing Sheets

(58) Field of Classification Search
CPC .............. A61M 5/31515; A61M 5/178; A61M 5/31511; A61M 2005/31508; A61M 2005/3101; A61M 5/315; A61M 5/31505; A61M 2005/31506

See application file for complete search history.

(56) References Cited

U.S. PATENT DOCUMENTS

| | | | |
|---|---|---|---|
| 6,368,306 | B1 | 4/2002 | Koska |
| 9,174,007 | B2 | 11/2015 | Lum et al. |
| 2006/0052748 | A1* | 3/2006 | Coelho ............... A61M 5/3216 604/110 |
| 2008/0300550 | A1 | 12/2008 | Schiller et al. |
| 2010/0076370 | A1* | 3/2010 | Howlett ............ A61M 5/31501 604/65 |
| 2014/0100532 | A1* | 4/2014 | Tennican .......... A61M 5/31596 604/218 |
| 2015/0080841 | A1 | 3/2015 | Bradley et al. |
| 2015/0119817 | A1* | 4/2015 | Prasad .............. A61M 5/31513 525/240 |
| 2017/0203046 | A1 | 7/2017 | LaRose |
| 2018/0200447 | A1 | 7/2018 | Furukawa |

FOREIGN PATENT DOCUMENTS

| | | | |
|---|---|---|---|
| JP | 2000514335 | A | 10/2000 |
| JP | 2002515268 | A | 5/2002 |
| JP | 2010184140 | A | 8/2010 |
| JP | 2010528773 | A | 8/2010 |
| WO | 9955402 | A1 | 11/1999 |
| WO | 2013070663 | A1 | 5/2013 |
| WO | 2017047295 | A1 | 3/2017 |

* cited by examiner

SYRINGE STOPPER AND PLUNGER ROD ARRANGEMENT FOR A SYRINGE ASSEMBLY

CROSS-REFERENCE TO RELATED APPLICATION

This application is the U.S. national phase of International Application No. PCT/US2019/022300 files Mar. 14,2019, and claims priority to United states Provisional Application Ser. No. 62/645,353, entitled "Syringe Stopper and Plunger Rod Arrangement for a Syringe Assembly", filed Mar. 20, 2018, the disclosures of which are hereby incorporated by reference in their entirety.

BACKGROUND OF THE INVENTION

Field of the Invention

The invention relates, in general, to a stopper assembly for use with a syringe and, more particularly, a stopper and plunger rod arrangement for use with a syringe.

Description of Related Art

Current syringe designs can typically be categorized as two-piece syringes or three-piece syringes. A typical three-piece syringe includes a tubular barrel having an access opening formed at one end, and a smaller discharge opening formed at the opposing end. The lead end of an elongated plunger is received within the access opening of the barrel so as to be slidable within the barrel. Attached to the lead end of the plunger is a flexible sealing member or stopper that snugly seals against the interior surface of the barrel. A needle, a threaded member, or a non-threaded member is usually attached to the discharge opening on the barrel. The needle can be used to penetrate a surface while the threaded member can be used to attach the syringe to another medical device, such as a catheter. The flexible stopper is usually manufactured from an elastomeric material, such as a rubber or a cross-linked or thermal plastic elastomer.

A two-piece syringe, on the other hand, includes a "stopper" that is in the form of a rigid sealing disc, also known as a plunger rod head. It is typically made of the same rigid plastic as the rest of the plunger rod. The sealing force in a two-piece syringe comes from a thin elastic barrel that deforms around the rigid plunger rod head.

During use, the discharge end of the syringe is initially placed in contact with a fluid. For example, the needle on the syringe can be inserted into a liquid medication. As the plunger is retracted within the barrel, a process known as aspiration, a negative pressure is formed within the end of the barrel so as to cause the fluid to be drawn into the barrel. The syringe can then be moved to a second location where advancing the plunger within the barrel causes the fluid to be pushed or expressed out of the discharge end of the barrel.

Current two-piece and three-piece syringe designs suffer from various deficiencies. In some instances, a syringe may be used during a high temperature autoclave sterilization process. An autoclave is typically used to sterilize surgical equipment, laboratory instruments, pharmaceutical items, and other materials. It can sterilize solids, liquids, hollows, and instruments of various shapes and sizes. An autoclave chamber sterilizes medical or laboratory instruments by heating them above boiling point. Steam is the autoclave's sterilization agent, which is typically produced at relatively high temperatures and pressures.

Typically, syringe designs that are subjected to high temperatures and pressures during an autoclave sterilization cycle use a vulcanized rubber for the stopper base material. There are, however, several significant disadvantages associated with using vulcanized rubber in syringe stopper applications that are used with an autoclave sterilization process. The bulk material cost of vulcanized rubber is significantly higher than alternative materials, such as thermal plastic elastomers. Further, the vulcanized rubber is more costly to manufacture in both capital equipment costs and production labor when compared to injectable moldable thermal plastic elastomers. The vulcanized rubber also has relatively higher chemical leachable characteristics that can negatively impact the medication stored in the syringe in comparison to thermal plastic elastomers.

Due to these disadvantageous characteristics, medical device manufacturer have begun using thermal plastic elastomer in prefilled autoclaved syringes. The thermal plastic elastomeric material, however, has a significantly lower resistance to high temperature compression set characteristics in comparison to the vulcanized rubber syringes. Therefore, the syringe stoppers made of the thermal plastic elastomeric material are designed with relatively low contact stress concentrations in order to have low yielding at high autoclave temperatures, which translates to acceptable fluid sealing robustness capabilities.

Some manufacturers have also accomplished the use of thermal plastic elastomeric material in the stoppers in part by using more complicated, multipart plunger rod designs in order to reduce plunger rod side loading transfer to the stopper. This effectively reduces stopper stress induced yielding and leakage. The multi-part syringe designs, however, tend to increase manufacturing and assembly costs. In addition, the multi-part plunger rod designs have a higher amount of mechanical backlash or play in both the axial and angular directions. This backlash has a less than optimal infusion positional control (feel) for the end user (clinician).

SUMMARY OF THE INVENTION

It is an object of the invention to provide an improved syringe stopper and plunger rod arrangement for use with thermal plastic elastomers. This improved arrangement is configured to better tolerate the high temperatures experienced by the arrangement during an autoclave sterilization process for increased syringe sealing performance robustness. The new arrangement makes it possible to use lower compression set performance materials such as thermal plastic elastomer resins for the syringe stopper, while still satisfying sterility, leakage, and other performance requirements necessary for a syringe. Utilizing thermal plastic elastomer resins for the syringe stopper significantly decreases bulk material costs, manufacturing costs, and leachable toxins to the syringe medication, as compared to traditional vulcanized rubber syringe stoppers.

To incorporate thermal plastic elastomers into syringe stoppers for use with autoclave syringes, the stopper stress concentrations can be reduced in order to reduce material yielding and increase sealing pressure. Further, the plunger rod side loading can be transferred directly from the plunger rod to the syringe barrel, thereby reducing asymmetric stopper deflection induced loading/leakage.

The stopper seal stress concentrations in the stopper ribs can be reduced to minimize localized stopper rib yielding during high temperature autoclave sterilization processing. This stress concentration reduction can be accomplished by balancing the stopper rib contact area with the internal structural features of the stopper and the overall barrel interference fit. The fluid sealing robustness can be increased by using fluid pressure during infusion with stopper cone internal support features. These support features allow the stopper cone to marginally collapse or slightly bend when the syringe fluid is under pressure. The cone bending causes the stopper cone base to apply radial loading on the stopper ribs, which increases the sealing contact pressure proportional to the syringe fluid pressure.

Angular misalignment of the stopper when the plunger rod is subjected to side loading can also be reduced by incorporating design features to limit the angular misalignment between the plunger rod and the barrel. The angular misalignment of the plunger rod can be further reduced by incorporating angular flex plunger rod design features between the plunger rod and the stopper. The angular flex features allow the plunger rod to barrel angular misalignment loading to be decoupled or significantly reduced at the plunger rod to stopper interface.

According to one aspect of the invention, the syringe assembly includes a substantially cylindrical syringe barrel including a fluid dispensing end, an open end, and at least one protrusion adjacent the open end, the at least one protrusion projecting inwardly from an inner surface of the syringe barrel, a stopper configured to be received within the open end of the syringe barrel, and a plunger rod having a plunger rod body extending along a longitudinal axis from a proximal end to a distal end and at least one support disk provided on the distal end thereof. The support disk on the plunger rod is configured to bear against the protrusion of the syringe barrel upon misalignment of the plunger rod in the syringe barrel. The at least one protrusion of the syringe barrel is a continuous rib that extends around an inner circumferential surface of the syringe barrel. The at least one support disk includes two support disks on the plunger rod spaced from one another such that, when the plunger rod is misaligned in the syringe barrel, a first support disk bears against a proximal side of the protrusion at a first load bearing point and a second support disk bears against a distal side of the protrusion at a second load bearing point. The plunger rod further includes a recess defined in the plunger rod body adjacent the support disk, the recess being defined by two protrusion members extending from an outer surface of the plunger rod body. Upon misalignment of the plunger rod in the syringe barrel, a first protrusion member bears against a proximal side of the protrusion at a first load bearing point, a second protrusion member bears against a distal side of the protrusion at a second load bearing point, and the support disk bears against the inner surface of the syringe barrel at a third load bearing point. The plunger rod further includes an attachment member provided on the distal end and configured for connection to the stopper. The support disk is spaced proximally from the attachment member. The plunger rod body further includes a rigid outer body member and a flexible inner body member provided within the rigid outer body member. The flexible inner body member is configured to flex upon misalignment of the plunger rod in the syringe barrel. The plunger rod body further includes an attachment member configured for connection with the stopper. The attachment member is provided on a distal end of the flexible inner body member. The at least one support disk includes two support disks on the plunger rod spaced from one another. Provided between the support disks, the plunger rod further includes a flexible region configured to flex upon misalignment of the plunger rod in the syringe barrel. The stopper includes a main body portion defining an open rearward end, a closed front end, and an inner cavity to receive the distal end of the plunger rod. An inner surface of the inner cavity defines a recess configured to act as a load bearing point for the plunger rod upon misalignment of the plunger rod within the syringe barrel. The stopper includes a main body portion defining an open rearward end, a closed front end, and an inner cavity to receive the distal end of the plunger rod. A portion of an inner surface of the inner cavity defines a plurality of notches configured to receive a plurality of projections extending from the distal end of the plunger rod body. Upon misalignment of the plunger rod in the syringe barrel, at least one projection on the plunger rod body bears against a corresponding notch in the inner cavity of the stopper at a load bearing point. The stopper is made of a thermal plastic elastomer.

In another aspect of the invention, the stopper adapted for attachment with a plunger rod for use within a syringe barrel includes a main body portion defining an open rearward end, a closed front end, and an inner cavity defined between the rearward end and the front end, the inner cavity defining an inner contour including a notch extending outwardly from an inner surface of the inner cavity, the notch separating a first contact surface of the inner contour from a second contact surface of the inner contour, a first rib extending from an outer surface of the main body portion and around an outer circumference of the main body portion, and a second rib spaced from the first rib, the second rib extending from an outer surface of the main body portion and around an outer circumference of the main body portion. A width of the first contact surface is substantially equal to a width of the first rib, and a width of the second contact surface is substantially equal to a width of the second rib. The notch defined in the inner contour provides a reduced thickness of the main body portion from the inner contour to an outer surface of the main body portion. The closed front end of the main body portion has a conical shape with a tip. A recess is formed on the outer surface of the main body portion between the first rib and the second rib. A width of the recess is substantially equal to a width of the notch. At least one collapsible cut-out is defined in the inner contour of the inner cavity. The collapsible cut-out permits the stopper to collapse or bend when under pressure. The stopper is made of a thermal plastic elastomer.

In another aspect of the invention, the plunger rod for use in a syringe assembly includes a plunger rod body extending along a longitudinal axis from a proximal end to a distal end, and at least two support disks provided on a distal end thereof. The support disks on the plunger rod are configured to bear against a protrusion on a syringe barrel upon misalignment of the plunger rod in the syringe barrel. An attachment member is provided on the distal end and configured for attachment to a stopper. The support disks are spaced proximally from the attachment member. The plunger rod further includes a recess defined in the plunger rod body adjacent the support disks. The recess is defined by two protrusion members extending from an outer surface of the plunger rod body. The plunger rod body further includes a rigid outer body member and a flexible inner body member provided within the rigid outer body member. The flexible inner body member is configured to flex upon misalignment of the plunger rod in the syringe barrel. The plunger rod body further includes an attachment member configured for connection with the stopper. The attachment member is provided on a distal end of the flexible inner body member. Provided between the support disks, the plunger rod further includes a flexible region configured to flex upon misalignment of the plunger rod in the syringe barrel.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DESCRIPTION OF THE INVENTION

For purposes of the description hereinafter, the terms "upper", "lower", "right", "left", "vertical", "horizontal", "up", "down", "lateral", "longitudinal", and derivatives thereof, shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting.

Figure 1:
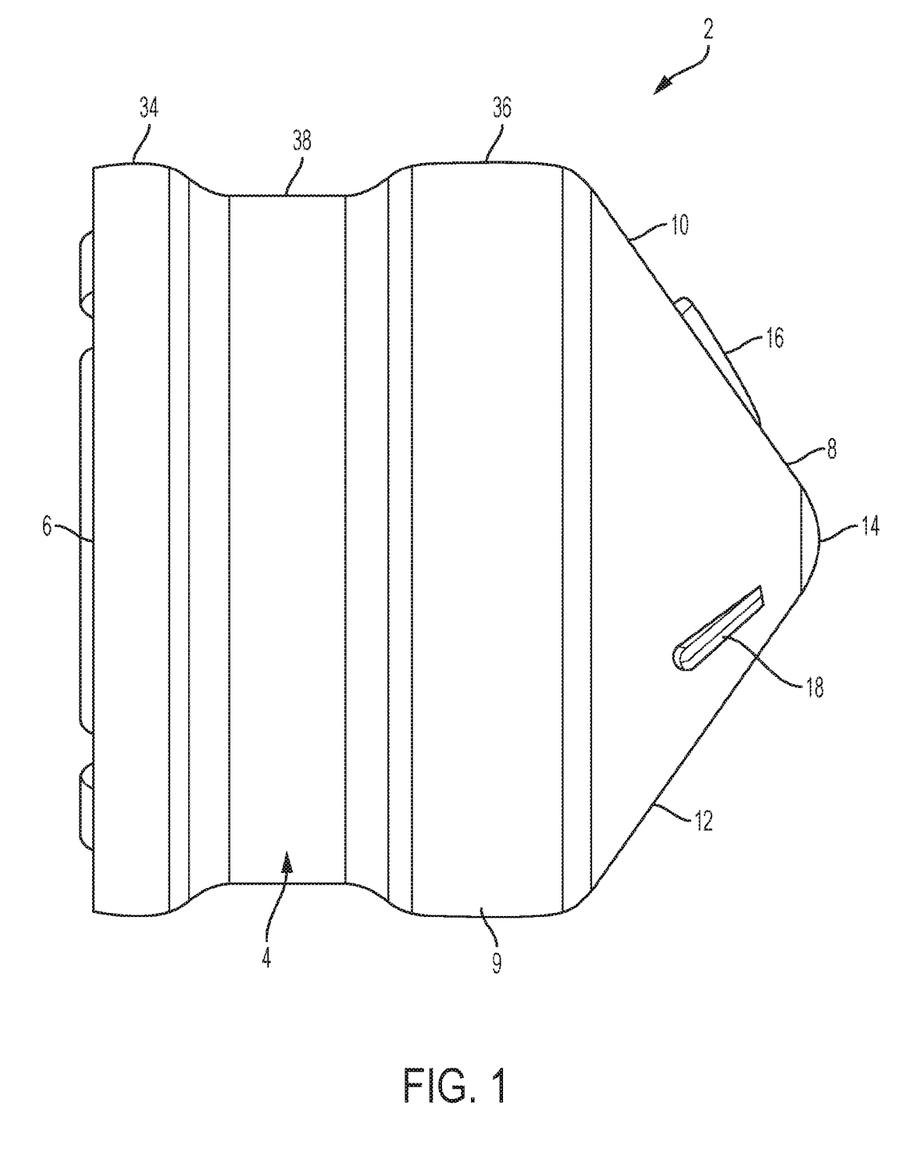
FIG. 1 is a side view of a stopper in accordance with an aspect of the present invention.
Figure 2:
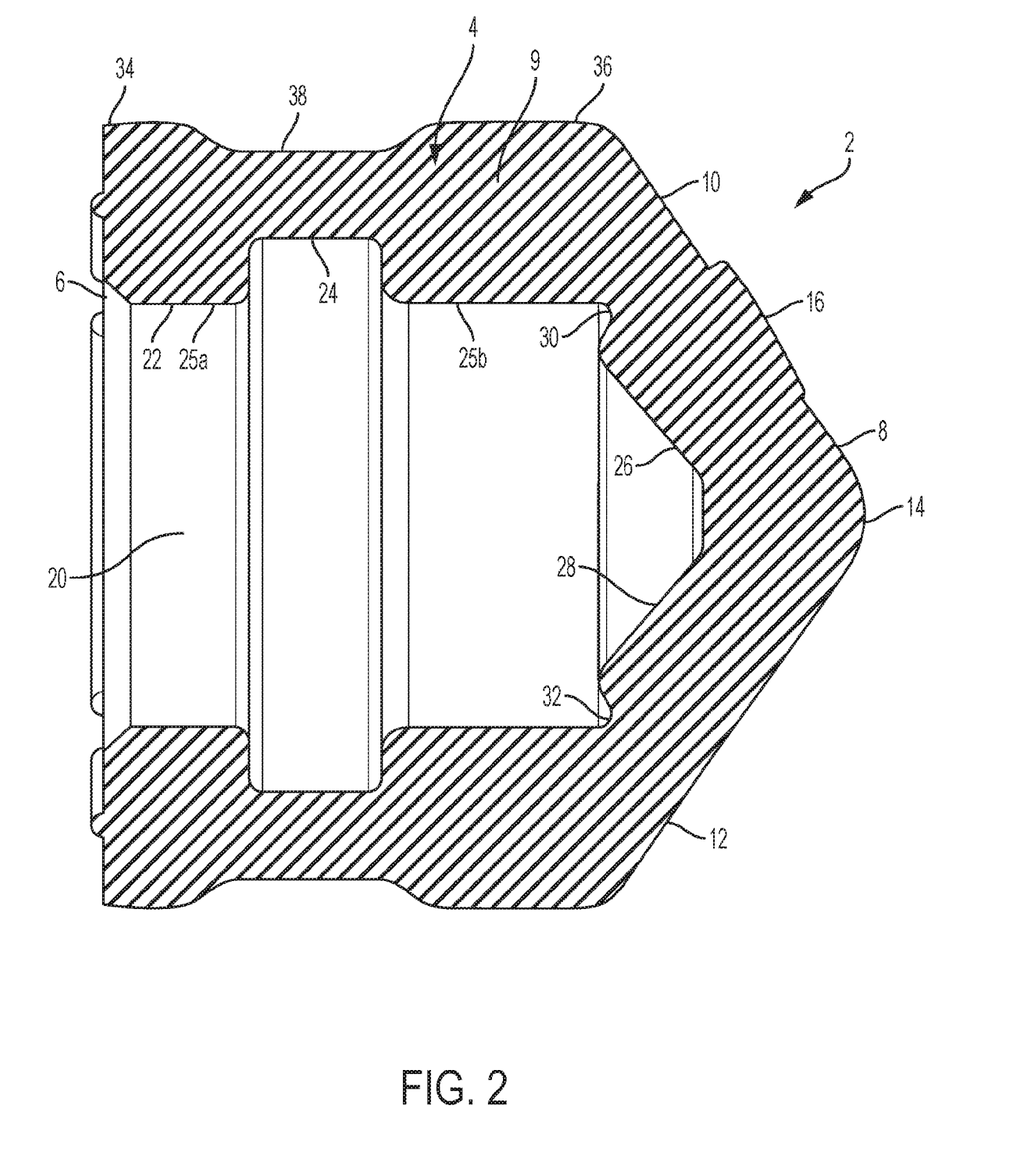
FIG. 2 is a side cross-sectional view of the stopper of FIG. 1.

With references to FIGS. 1 and 2, a first aspect of the stopper 2 includes a main body portion 4 defining an open rearward end 6 configured to receive a plunger rod and a closed front end 8 that forms a flexible roof. In one aspect, the stopper 2 is made of a thermal plastic elastomer. It is also contemplated that the stopper 2 is made of any alternative hard or soft plastic. The closed front end 8 of the main body portion 4 includes a substantially cylindrical portion 9, a first angled portion 10 and a second angled portion 12, which are both part of a single conical surface, that extend toward a tip 14, thereby providing the closed front end 8 with a substantially conical appearance. However, this shape of the flexible roof is not to be considered as limiting the present invention as the roof may be flat. Such a roof would not provide flexing roof action in which a flexible roof of the stopper flexes inward and expands sideways in a radial direction. As shown in FIG. 1, at least dimple 16, 18 extends from an outer surface of the first angled portion 10 and the second angled portion 12 of the closed front end 8. Dimples 16, 18 are designed to keep the stopper 2 from making contact with a front portion of the syringe barrel for preventing reflux flow at the end of an injection procedure. Although only one dimple 16, 18 is shown extending from the first angled portion 10 and the second angled portion 12, it is contemplated that additional features may be provided on these surfaces or no dimples may be provided on these surfaces.

As shown in FIG. 2, the main body portion 4 of the stopper 2 is substantially hollow and designed to receive an attachment portion of a plunger rod, as described below. The main body portion 4 of the stopper 2 defines an inner cavity 20 that receives the attachment portion of the plunger rod. The inner cavity 20 is defined between the rearward end 6 and the closed front end 8 of the main body portion 4. The inner cavity 20 defines an inner contour 22 in the main body portion 4. The inner contour 22 defines a notch 24 configured to receive a portion of the attachment portion of the plunger rod to retain the attachment portion within the inner cavity 20. The notch 24 is defined in the cylindrical portion 9 of the main body portion 4 and extends outwardly from the inner surface of the inner cavity 20 and around the circumferential surface of the inner contour 22. The notch 24 defined in the inner contour 22 defines a reduced thickness of the main body portion 4 from the inner contour 22 to the outer surface of the main body portion 4 as compared to the thickness in the remaining portion of the main body portion 4. The notch 24 is defined between a first contact surface 25a and a second contact surface 25b of the inner contour 22. The reduction in thickness of the cylindrical portion 9 assists in reducing plunger rod misalignment loading forces transferring to the stopper rib contact surfaces.

The inner contour 22 of the inner cavity 20 also defines a first angled portion 26 and a second angled portion 28 in the front end 8 of the stopper 2 that correspond to the first angled portion 10 and the second angled portion 12 of the outer surface of the front end 8. The first angled portion 26 and the second angled portion 28, which are both part of a single conical surface, provide the inner surface of the closed front end 8 with a substantially conical appearance. Adjacent the first angled portion 26 and the second angled portion 28, a pair of collapsible cut-outs 30, 32 are defined in the inner contour 22. The collapsible cut-outs 30, 32 are notches or recesses defined in the inner contour 22 of the main body portion 4. The collapsible cut-outs 30, 32 are provided to allow the adjacent portions of the main body portion 4 to bend radially outward when the stopper is under fluid pressure, which causes the flexible roof of the front end 8 to bend axially inward in an aft direction. The portions of the main body portion 4 that are bent radially outward assist in keeping the outer surface of the main body portion 4 in contact with the inner surface of the syringe barrel in which the stopper 2 is moving to improve the interference fit between the stopper 2 and the syringe barrel so that the sealing contact pressure between the stopper 2 and the syringe barrel is proportional to the syringe fluid pressure acting on the stopper 2.

With reference to FIGS. 1 and 2, the outer surface of the cylindrical portion 9 of the main body portion 4 includes a first rib 34 provided adjacent the rearward end 6 and a second rib 36 adjacent the front end 8 of the main body portion 4. In one aspect, the ribs 34, 36 extend around the entire circumferential outer surface of the cylindrical portion 9. In another aspect, the ribs 34, 36 are provided in segments around the circumferential outer surface of the cylindrical portion 9. The ribs 34, 36 extend outwardly from the outer surface of the cylindrical portion 9 to act as bearing points against the inner surface of the syringe barrel. The first rib 34 is spaced from the second rib 36 on the cylindrical portion 9. As shown in FIG. 2, a width of the first rib 34 is substantially equal to a width of the first contact surface 25*a* of the inner contour 22. A width of the second rib 36 is substantially equal to a width of the second contact surface 25*b* of the inner contour 22. Since the widths of the ribs 34, 36 are substantially equal to the widths of the contact surfaces 25*a*, 25*b* of the inner contour 22, a balanced support of the ribs 34, 36 against the inner surface of the syringe barrel is achieved. This feature assists in reducing the stopper seal stress concentrations within the stopper 2. This stress concentration reduction thereby reduces the localized stopper rib yielding during high temperature autoclave sterilization processing. The reduction in material yielding translates to increased passive sealing robustness capabilities for the stopper 2. The first rib 34 and the second rib 36 of the cylindrical portion 9 form a recess 38 on the outer surface of the main body portion 4. The width of the recess 38 is substantially equal to the width of the notch 24 defined in the inner contour 22. The surface of the recess 38 is not in contact with the inner surface of the syringe barrel.

Figure 3:
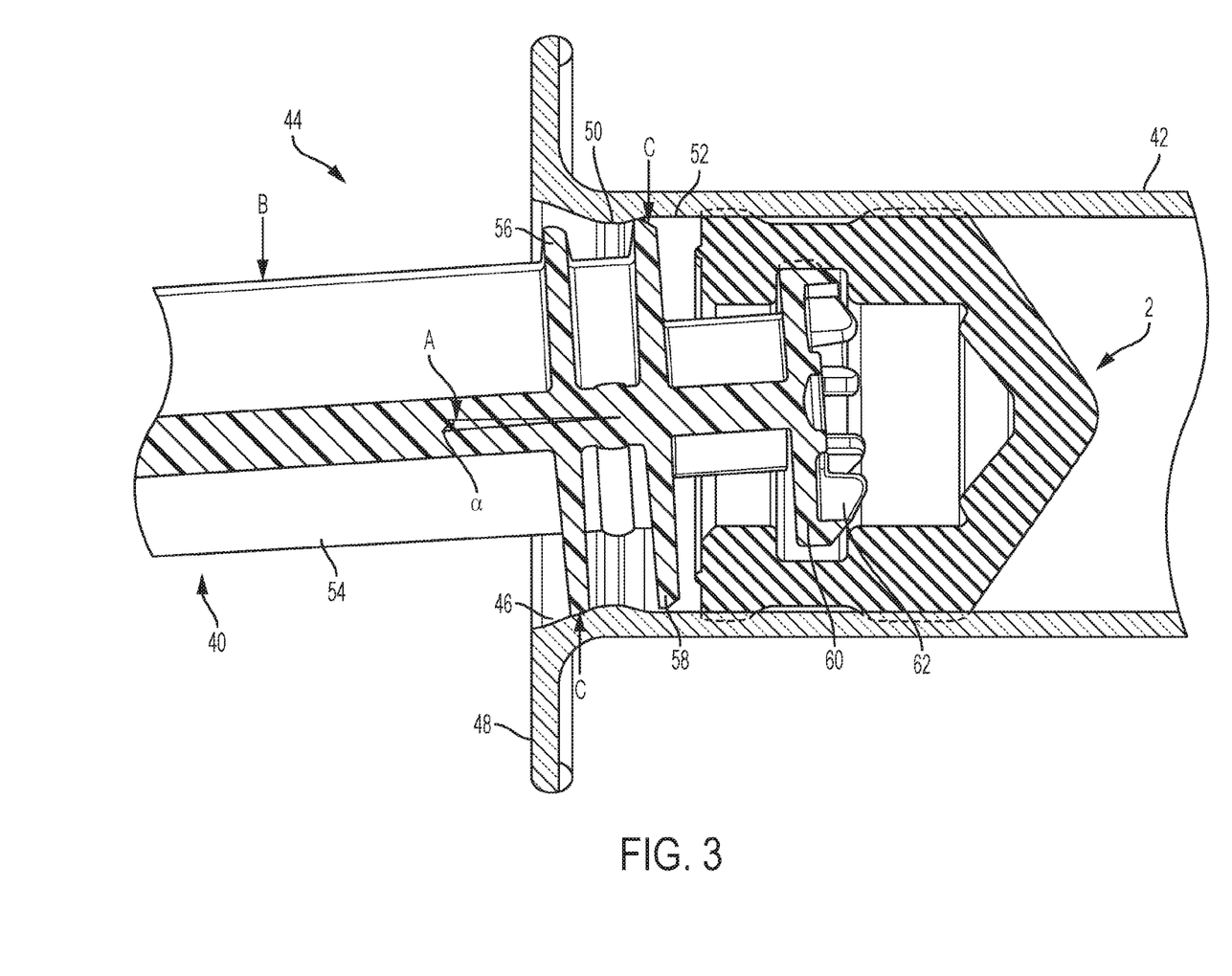
FIG. 3 is a side cross-sectional view of a plunger rod, the stopper of FIG. 1, and a syringe barrel in accordance with another aspect of the present invention.

With reference to FIG. 3, the stopper 2 is shown in use with a plunger rod 40 and a syringe barrel 42 to form a syringe assembly 44. The stopper 2 and the plunger rod 40 are adapted for use with the syringe barrel 42. The syringe barrel 42 is made of medical-grade plastic or glass. The plunger rod 40 is made of a medical-grade plastic. The syringe barrel 42 is substantially cylindrical and extends from an open proximal end 46 to a distal dispensing end (not shown) from which fluid is ejected during use of the syringe assembly 44. The distal dispensing end includes an outlet opening and/or a mechanism (such as a luer fitting) for attachment to a separate medical device (such as a catheter). The open end 46 is configured to receive the stopper 2 and the plunger rod 40. A flange 48 is provided around the circumferential surface of the open end 46. At least one protrusion 50 projects inwardly from an inner surface 52 of the syringe barrel 42. In one aspect, the protrusion 50 extends around the entire circumferential surface of the inner surface 52 of the syringe barrel 42. In another aspect, the protrusion 50 is provided as a plurality of segments that extend around the circumferential surface of the inner surface 52. The protrusion 50 is provided adjacent the open end 46 of the syringe barrel 42. It is also contemplated that additional protrusions may be provided on the syringe barrel 42 at a distal position from the protrusion 50.

The plunger rod 40 is operatively connected to the stopper 2, such that, upon depression of the plunger rod 40 in a distal direction, the stopper 2 is moved in a distal direction within the syringe barrel 42 to direct the fluid out of the dispensing end of the syringe barrel 42. The plunger rod 40 includes a main body portion 54, at least one support disk 56, 58, and an attachment member 60. The main body portion 54 includes a proximal end having an actuator button or tab (not shown) for moving the plunger rod 40 in a distal or proximal direction, and a distal end upon which the support disks 56, 58 are formed. The support disks 56, 58 extend outwardly from the distal end of the main body portion 54 and are substantially circular in shape to correspond to the shape of the syringe barrel 42. It is contemplated, however, that the support disks 56, 58 can have alternative shapes that are accommodated in the syringe barrel 42. The first support disk 56 is spaced proximally from the second support disk 58 on the distal end of the main body portion 54. The support disks 56, 58 have substantially the same diameter.

The attachment member 60 of the plunger rod 40 is provided on the distal end of the plunger rod 40 and is spaced distally from the support disks 56, 58 on the plunger rod 40. The attachment member 60 has a smaller diameter than the support disks 56, 58. The attachment member 60 also includes at least one gripping protrusion 62 that extends distally from the attachment member 60. The gripping protrusions 62 are configured to assist in gripping the stopper 2 upon insertion of the attachment member 60 into the inner cavity 20 of the stopper 2. During use, the plunger rod 40 is pushed in a distal direction into the open rearward end 6 of the stopper 2 so that the attachment member 60 is inserted into the inner cavity 20 of the stopper 2. As the plunger rod 40 is moved in the distal direction, the attachment member 60 is moved into the notch 24 defined in the inner contour 22 of the stopper 2. Using this interconnection between the attachment member 60 and the notch 24, the plunger rod 40 is retained in the stopper 2 such that the stopper 2 and plunger rod 40 move in conjunction with one another in the syringe barrel 42. It is also contemplated that the plunger rod 40 is molded integrally with the stopper 2 to form this arrangement. Since the diameter of the notch 24 is larger than the diameter of the attachment member 60, the plunger rod 40 is permitted to rotate relative to the stopper 2.

As shown in FIG. 3, during use of the syringe assembly 44, the plunger rod 40 may become misaligned relative to a longitudinal axis A of the syringe assembly 44 that extends through the syringe barrel 42, the stopper 2, and the plunger rod 40. Misalignment of the plunger rod 40 can occur due to a clinician's thumb load misalignment on the plunger rod 40 with respect to the longitudinal axis A of the syringe assembly. Due to a side loading force B on the plunger rod 40, the plunger rod 40 may be rotated at an angle $\alpha$ relative to the longitudinal axis A of the syringe assembly 44. Based on this side loading force B, the attachment member 60 of the plunger rod 40 rotates within the stopper 2 causing stress concentrations in parts of the stopper 2. Due to these stress concentrations, the seal between the stopper 2 and the syringe barrel 42 may be deteriorated or the material of the stopper 2 may be worn down under high temperatures. To reduce the effects of the misalignment of the plunger rod 40, the support disks 56, 58 are configured to bear against the protrusion 50 extending from the inner surface 52 of the syringe barrel 42. Upon rotation of the plunger rod 40 relative to the longitudinal axis A, the proximal support disk 56 is configured to bear against a proximal side of the protrusion 50, and the distal support disk 58 is configured to bear against a distal side of the protrusion 50. The protrusion 50 acts as a bearing point for the support disks 56, 58 to limit the amount of rotation of the plunger rod 40 and to reduce the bearing force exerted by the attachment member 60 within the stopper 2. Using the protrusion 50 as a bearing point causes a significant portion of the side loading force B to be transferred directly from the plunger rod 40 to the syringe barrel 42 as a barrel reactive loading force C, which results in a reduced loading force that is transferred from the plunger rod 40 to the stopper 2. The reduced loading force on the side of the stopper 2 reduces asymmetric stopper deflection-induced loading/leakage in the seal between the stopper 2 and the syringe barrel 42.

Figure 4:
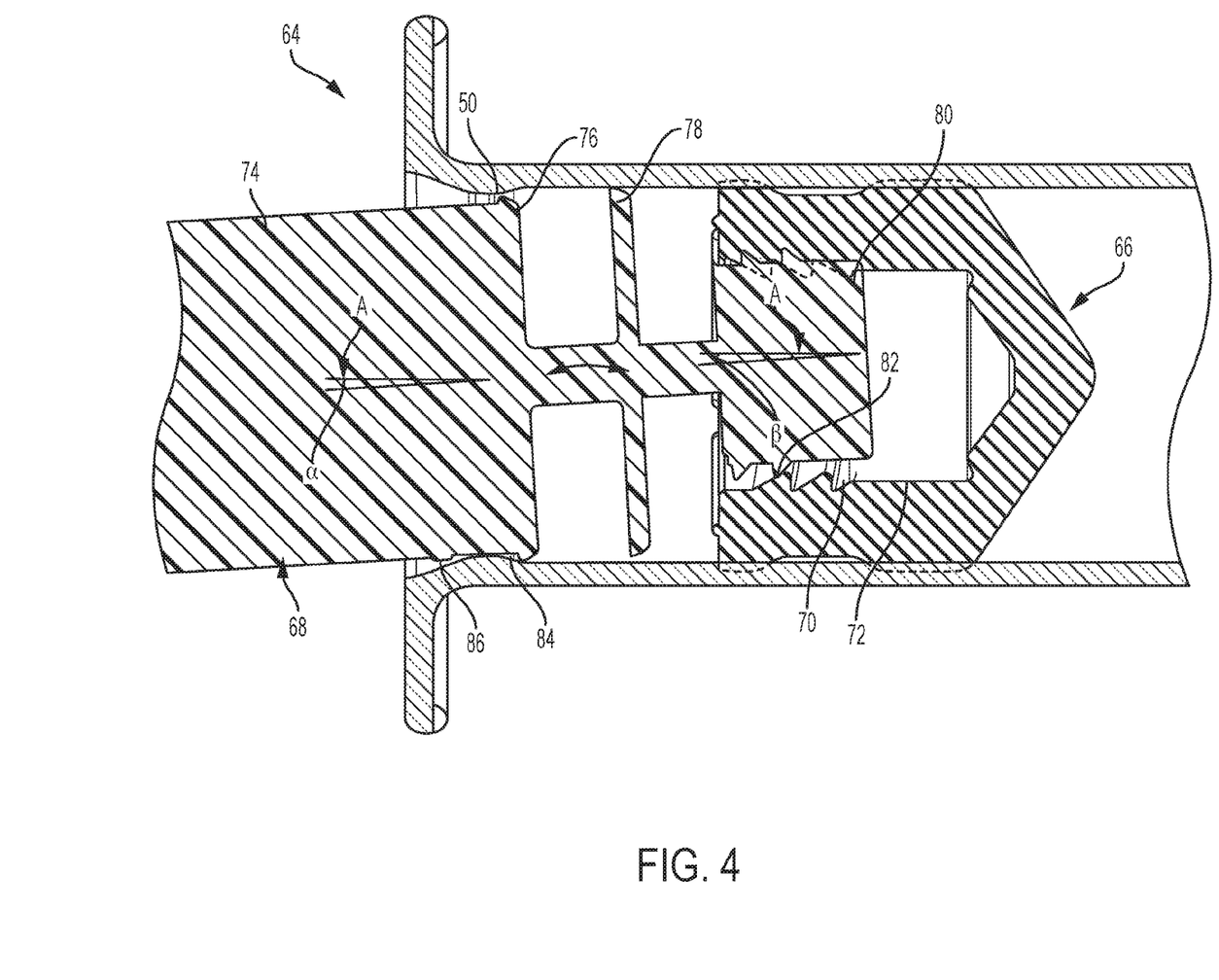
FIG. 4 is a side cross-sectional view of a plunger rod, stopper, and syringe barrel in accordance with another aspect of the present invention.

With reference to FIG. 4, another aspect of the syringe assembly 64 is shown. In this aspect, the syringe barrel 42 is the same as that described in the syringe assembly 44 of FIG. 3. The stopper 66 and the plunger rod 68 of this aspect, however, are slightly different from the stopper 2 and the plunger rod 40 of the syringe assembly 44 shown in FIG. 3. The stopper 66 has all of the same features as the stopper 2 of FIG. 3, except the stopper 66 does not include a notch similar to the notch 24 in the stopper 2. Instead, the stopper 66 defines a plurality of notches 70 in an inner contour 72 of the stopper 66.

The plunger rod 68 includes a main body portion 74, at least one support disk 76, 78, and an attachment member 80 configured to connect with the stopper 66. The attachment member 80 is provided on a distal end of the plunger rod 68 and is distally spaced from the support disks 76, 78. The attachment member 80 has a diameter smaller than the support disks 76, 78 and an inner cavity of the stopper 66. A plurality of protrusions 82 are provided on the circumferential outer surface of the attachment member 80 and are configured to connect the attachment member 80 within the stopper 66. The protrusions 82 are substantially triangular and correspond in shape to the notches 70 defined in the stopper 66. Therefore, as the plunger rod 68 is moved distally towards the stopper 66, the attachment member 80 is inserted into the inner cavity of the stopper 66. As the attachment member 80 moves in a distal direction within the inner cavity of the stopper 66, the protrusions 82 are moved from a first notch 70 to a second notch 70 within the stopper 66. The notches 70 allow for distal movement of the attachment member 80 within the stopper 66, but prevent proximal movement of the attachment member 80 out of the stopper 66.

With continued reference to FIG. 4, a recess 84 is defined in the main body portion 74 of the plunger rod 68. The recess 84 is defined proximally from the first support disk 76. The recess 84 is formed between the first support disk 76 and a protrusion 86 that extends from the main body portion 74. The recess 84 assists in reducing the bearing load transferred to the stopper 66 upon misalignment of the plunger rod 68 within the syringe barrel 42. Upon assembly of the plunger rod 68 in the syringe barrel 42, the plunger rod 68 is moved distally within the syringe barrel 42 until the protrusion 50 on the syringe barrel 42 is positioned within the recess 84 of the plunger rod 68. Upon misalignment of the plunger rod 68 within the syringe barrel 42 due to a side bearing load on the plunger rod 68, the plunger rod 68 is rotated at an angle α from the longitudinal axis A of the syringe assembly 64. Once the plunger rod 68 has been rotated, the distal end of the protrusion 86 bears against the proximal side of the protrusion 50 of the syringe barrel 42, and a proximal side of the first support disk 76 bears against a distal side of the protrusion 50. Further, the second support disk 78 may bear against the inner surface of the syringe barrel 42. The protrusions 82 of the attachment member 80 also bear against the notches 70 defined in the stopper 66.

The plunger rod 68 also includes a flexible region 88 between the first support disk 76 and the second support disk 78. In one aspect, the flexible region 88 is more flexible than the remaining portions of the plunger rod 68. Due to the flexibility of the flexible region 88, upon misalignment of the plunger rod 68, the angle of misalignment of the attachment member 80 within the stopper 66 is reduced. In particular, since the flexible region 88 is permitted to flex and rotate with the misalignment of the plunger rod 68, the side bearing load is not fully transferred to the attachment portion 80, which rotates a smaller angle than the main body portion 74 of the plunger rod 68. In particular, the angle of rotation R of the attachment member 80 is less than the angle of rotation a of the main body portion 74. Due to the smaller rotation of the attachment member 80 within the stopper 66, the side loading force from the attachment member 80 applied to the stopper 66 is reduced. This reduction in side loading force on the stopper 66 reduces deflection-induced leakage on the sealing surface between the stopper 66 and the inner surface of the syringe barrel 42.

Figure 5:
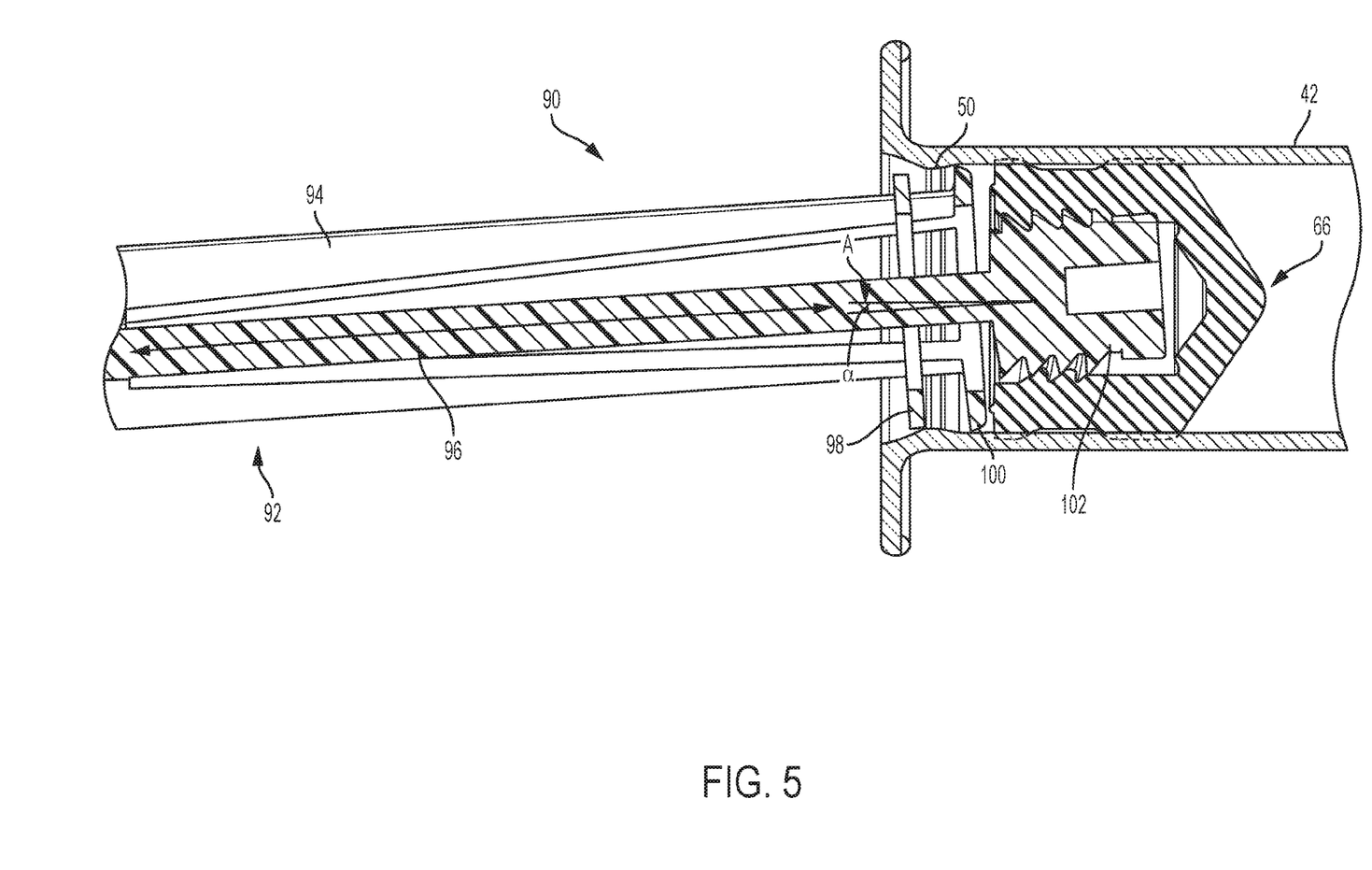
FIG. 5 is a side cross-sectional view of the plunger rod, stopper, and syringe barrel of FIG. 4 shown in a flexed position.

With reference to FIG. 5, another aspect of a syringe assembly 90 is shown. The syringe assembly 90 includes a stopper 66, a syringe barrel 42, and a plunger rod 92. The stopper 66 is the same stopper 66 disclosed in FIG. 4. The syringe barrel 42 is the same syringe barrel 42 disclosed in FIGS. 3 and 4. The plunger rod 92, however, includes several features that are not provided in the plunger rod 40 of FIG. 3 and the plunger rod 68 of FIG. 4. The plunger rod 92 includes at least one outer body member 94, an inner body member %, at least one support disk 98, 100, and an attachment member 102 for connection of the plunger rod 92 to the stopper 66. In one aspect, a plurality of outer body member 94 surround the inner body member 96. The outer body members 94 are made of a rigid plastic material, and the inner body member 96 is made of a flexible plastic material. The inner body member 96 extends within the outer body member 94. Upon misalignment of the plunger rod 92 due to a side bearing load on the plunger rod 92, the inner body member % is configured to flex to reduce the angle of rotation a of the plunger rod 92 within the syringe barrel 42. The outer body members 94 remain rigid during rotation of the plunger rod 92. In one aspect, the attachment member 102 is formed on a distal end of the inner body member % so that, due to the flexion of the inner body member 96 during misalignment of the plunger rod 92, the amount of side bearing load transferred from the attachment member 102 to the stopper 66 is reduced. During misalignment of the plunger rod 92, the inner body member % experiences significant deflection, while the outer body member 94 remains rigid. The rigid outer body member 94 is designed to transfer a large portion of the side bearing load from the plunger rod 92 to the syringe barrel 42 through the support disks 98, 100 bearing against the protrusion 50 on the syringe barrel 42, as described hereinabove.

While specific aspects of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

The invention claimed is:

1. A syringe assembly, comprising:
   a) a substantially cylindrical syringe barrel comprising a fluid dispensing end, an open end, and at least one protrusion adjacent the open end, the at least one protrusion projecting inwardly from an inner surface of the syringe barrel;
   b) a stopper configured to be received within the open end of the syringe barrel; and
   c) a plunger rod having a plunger rod body extending along a longitudinal axis from a proximal end to a distal end and at least one support disk provided on the distal end thereof,
   wherein the at least one support disk on the plunger rod is configured to bear against the at least one protrusion of the syringe barrel upon misalignment of the plunger rod in the syringe barrel,
   wherein the at least one support disk comprises a first support disk and a second support disk on the plunger rod spaced from one another such that, when the plunger rod is misaligned in the syringe barrel, the first support disk bears against a proximal side of at least one the protrusion at a first load bearing point and the second support disk bears against a distal side of the at least one protrusion at a second load bearing point.

2. The syringe assembly of claim 1, wherein the at least one protrusion of the syringe barrel is a continuous rib that extends around an inner circumferential surface of the syringe barrel.

3. The syringe assembly of claim 1,
wherein the plunger rod further comprises an attachment member provided on the distal end and configured for connection to the stopper, and
wherein the at least one support disk is spaced proximally from the attachment member.

4. The syringe assembly of claim 1, wherein the plunger rod body further comprises a rigid outer body member and a flexible inner body member provided within the rigid outer body member, the flexible inner body member being configured to flex upon misalignment of the plunger rod in the syringe barrel.

5. The syringe assembly of claim 4, wherein the plunger rod body further comprises an attachment member configured for connection with the stopper, the attachment member being provided on a distal end of the flexible inner body member.

6. The syringe assembly of claim 1,
wherein the stopper comprises a main body portion defining an open rearward end, a closed front end, and an inner cavity to receive the distal end of the plunger rod, and
wherein an inner surface of the inner cavity defines a recess configured to act as a load bearing point for the plunger rod upon misalignment of the plunger rod within the syringe barrel.

7. The syringe assembly of claim 1,
wherein the stopper comprises a main body portion defining an open rearward end, a closed front end, and an inner cavity to receive the distal end of the plunger rod,
wherein a portion of an inner surface of the inner cavity defines a plurality of notches configured to receive a plurality of projections extending from the distal end of the plunger rod body, and
wherein, upon misalignment of the plunger rod in the syringe barrel, at least one projection on the plunger rod body bears against a corresponding notch in the inner cavity of the stopper at a load bearing point.

8. The syringe assembly of claim 1, wherein the stopper is made of a thermal plastic elastomer.

9. The syringe assembly of claim 1, wherein the stopper comprises:
a main body portion defining an open rearward end, a closed front end, and an inner cavity defined between the rearward end and the front end, the inner cavity defining an inner contour including a notch extending outwardly from an inner surface of the inner cavity, the notch separating a first contact surface of the inner contour from a second contact surface of the inner contour;
a first rib extending from an outer surface of the main body portion and around an outer circumference of the main body portion; and
a second rib spaced from the first rib, the second rib extending from an outer surface of the main body portion and around an outer circumference of the main body portion,
wherein a width of the first contact surface is substantially equal to a width of the first rib, and a width of the second contact surface is substantially equal to a width of the second rib.

10. The syringe assembly of claim 9, wherein the notch defined in the inner contour provides a reduced thickness of the main body portion from the inner contour to an outer surface of the main body portion.

11. The syringe assembly of claim 9, wherein the closed front end of the main body portion has a conical shape with a tip.

12. The syringe assembly of claim 9, wherein a recess is formed on the outer surface of the main body portion between the first rib and the second rib, a width of the recess being substantially equal to a width of the notch.

13. The syringe assembly of claim 9, wherein at least one collapsible cut-out is defined in the inner contour of the inner cavity, wherein the collapsible cut-out permits the stopper to collapse or bend when under pressure.

14. The syringe assembly of claim 9, wherein the stopper is made of a thermal plastic elastomer.

15. A syringe assembly, comprising:
a) a substantially cylindrical syringe barrel comprising a fluid dispensing end, an open end, and at least one protrusion adjacent the open end, the at least one protrusion projecting inwardly from an inner surface of the syringe barrel;
b) a stopper configured to be received within the open end of the syringe barrel; and
c) a plunger rod having a plunger rod body extending along a longitudinal axis from a proximal end to a distal end and at least one support disk provided on the distal end thereof,
wherein the at least one support disk on the plunger rod is configured to bear against the at least one protrusion of the syringe barrel upon misalignment of the plunger rod in the syringe barrel,
wherein the plunger rod further comprises a recess defined in the plunger rod body adjacent the at least one support disk, the recess being defined by a first protrusion member and a second protrusion member extending from an outer surface of the plunger rod body, and
wherein, upon misalignment of the plunger rod in the syringe barrel, the first protrusion member bears against a proximal side of the at least one protrusion at a first load bearing point, the second protrusion member bears against a distal side of the at least one protrusion at a second load bearing point, and the at least one support disk bears against the inner surface of the syringe barrel at a third load bearing point.

16. A syringe assembly, comprising:
a) a substantially cylindrical syringe barrel comprising a fluid dispensing end, an open end, and at least one protrusion adjacent the open end, the at least one protrusion projecting inwardly from an inner surface of the syringe barrel;
b) a stopper configured to be received within the open end of the syringe barrel; and
c) a plunger rod having a plunger rod body extending along a longitudinal axis from a proximal end to a distal end and at least one support disk provided on the distal end thereof,
wherein the at least one support disk on the plunger rod is configured to bear against the at least one protrusion of the syringe barrel upon misalignment of the plunger rod in the syringe barrel, wherein the at least one support disk comprises two support disks on the plunger rod spaced from one another, and wherein, provided between the two support disks, the plunger rod further comprises a flexible region configured to flex upon misalignment of the plunger rod in the syringe barrel.

\* \* \* \* \*

UNITED STATES PATENT AND TRADEMARK OFFICE
CERTIFICATE OF CORRECTION

| | |
|---|---|
| PATENT NO. | : 11,701,472 B2 |
| APPLICATION NO. | : 16/977904 |
| DATED | : July 18, 2023 |
| INVENTOR(S) | : Ryan |

It is certified that error appears in the above-identified patent and that said Letters Patent is hereby corrected as shown below:

In the Specification

Column 1, Line 9, delete "files" and insert -- filed --

Column 1, Line 10, delete "states" and insert -- States --

In the Claims

Column 10, Line 67, Claim 1, after "side of" insert -- the --

Column 11, Line 1, Claim 1, after "one" delete "the"

Signed and Sealed this
Twelfth Day of September, 2023

Katherine Kelly Vidal
*Director of the United States Patent and Trademark Office*